United States Patent
Jeffrey

(10) Patent No.: US 10,485,935 B2
(45) Date of Patent: Nov. 26, 2019

(54) NEEDLE RETRACTION MEDICAL DEVICE

(71) Applicant: SAFE-T LIMITED, Ballasalla (GB)

(72) Inventor: Peter Jeffrey, Ballasalla (GB)

(73) Assignee: SAFE-T LIMITED, Ballasalla (GB)

( * ) Notice: Subject to any disclaimer, the term of this patent is extended or adjusted under 35 U.S.C. 154(b) by 258 days.

(21) Appl. No.: 15/546,433

(22) PCT Filed: Jan. 25, 2016

(86) PCT No.: PCT/GB2016/050149
§ 371 (c)(1),
(2) Date: Jul. 26, 2017

(87) PCT Pub. No.: WO2016/120595
PCT Pub. Date: Aug. 4, 2016

(65) Prior Publication Data
US 2018/0008786 A1  Jan. 11, 2018

(30) Foreign Application Priority Data
Jan. 27, 2015  (GB) ..................................... 1501317

(51) Int. Cl.
*A61M 5/32* (2006.01)
*A61M 5/50* (2006.01)

(52) U.S. Cl.
CPC ........ *A61M 5/3234* (2013.01); *A61M 5/3202* (2013.01); *A61M 5/50* (2013.01);
(Continued)

(58) Field of Classification Search
CPC ........ A61M 5/3234; A61M 2005/3235; A61M 2005/3241
See application file for complete search history.

(56) References Cited

U.S. PATENT DOCUMENTS

| 5,407,436 A | * | 4/1995 | Toft | ...................... | A61M 5/315 |
| | | | | | 604/110 |
| 5,685,743 A | | 11/1997 | Schmidt et al. | | |
| 6,783,003 B2 | * | 8/2004 | Simm | ................... | A61M 5/008 |
| | | | | | 206/366 |

FOREIGN PATENT DOCUMENTS

| EP | 0 711 002 A2 | 5/1996 |
| EP | 1 291 029 A1 | 3/2003 |

(Continued)

OTHER PUBLICATIONS

International Search Report and Written Opinion for International Application No. PCT/GB2016/050149, dated Mar. 23, 2016.
(Continued)

*Primary Examiner* — Laura A Bouchelle
(74) *Attorney, Agent, or Firm* — Wolf, Greenfield & Sacks, P.C.

(57) ABSTRACT

A needle retraction medical device including a hollow body (10) and a plunger (20). The hollow body (10) has a first end (11) provided with a needle mounting hub (13) and a plurality of releasable latches (15) holding the needle mounting hub (13) against spring (14) bias. The latches (15) are formed integrally with the hollow body (10) and project longitudinally inside the hollow body (10) from a proximal end at or adjacent the first end (11) of the hollow body (10) to a free end. A respective opening (35) is provided in the body (10) radially inwards of each of the latches (15). The plunger (20) has a forward end insertable into the body (10) from a second end thereof, a hollow interior and a closed rear end. The plunger front end is operable, upon insertion of the plunger (20) into the body (10), to deflect the latches (15) radially outwards and thereby release the needle mounting hub (13) from the latches (15) so that the hub (13) together with the needle mounted thereby retract under spring action into the hollow interior of the plunger (20). A (Continued)

respective opening (30) is also provided in the hollow body (10) radially outwards of at least some of the latches (15) so that each such latch (15) connects to the material of the body (10) only at each side of its proximal end.

18 Claims, 15 Drawing Sheets

(52) U.S. Cl.
  CPC ............... *A61M 2005/3236* (2013.01); *A61M 2005/3241* (2013.01)

(56) References Cited

FOREIGN PATENT DOCUMENTS

| | | |
|---|---|---|
| WO | WO 92/18187 A1 | 10/1992 |
| WO | WO 93/12830 A1 | 7/1993 |
| WO | WO 96/32977 A1 | 10/1996 |

OTHER PUBLICATIONS

International Preliminary Report on Patentability for International Application No. PCT/GB2016/050149, dated Aug. 10, 2017.

\* cited by examiner

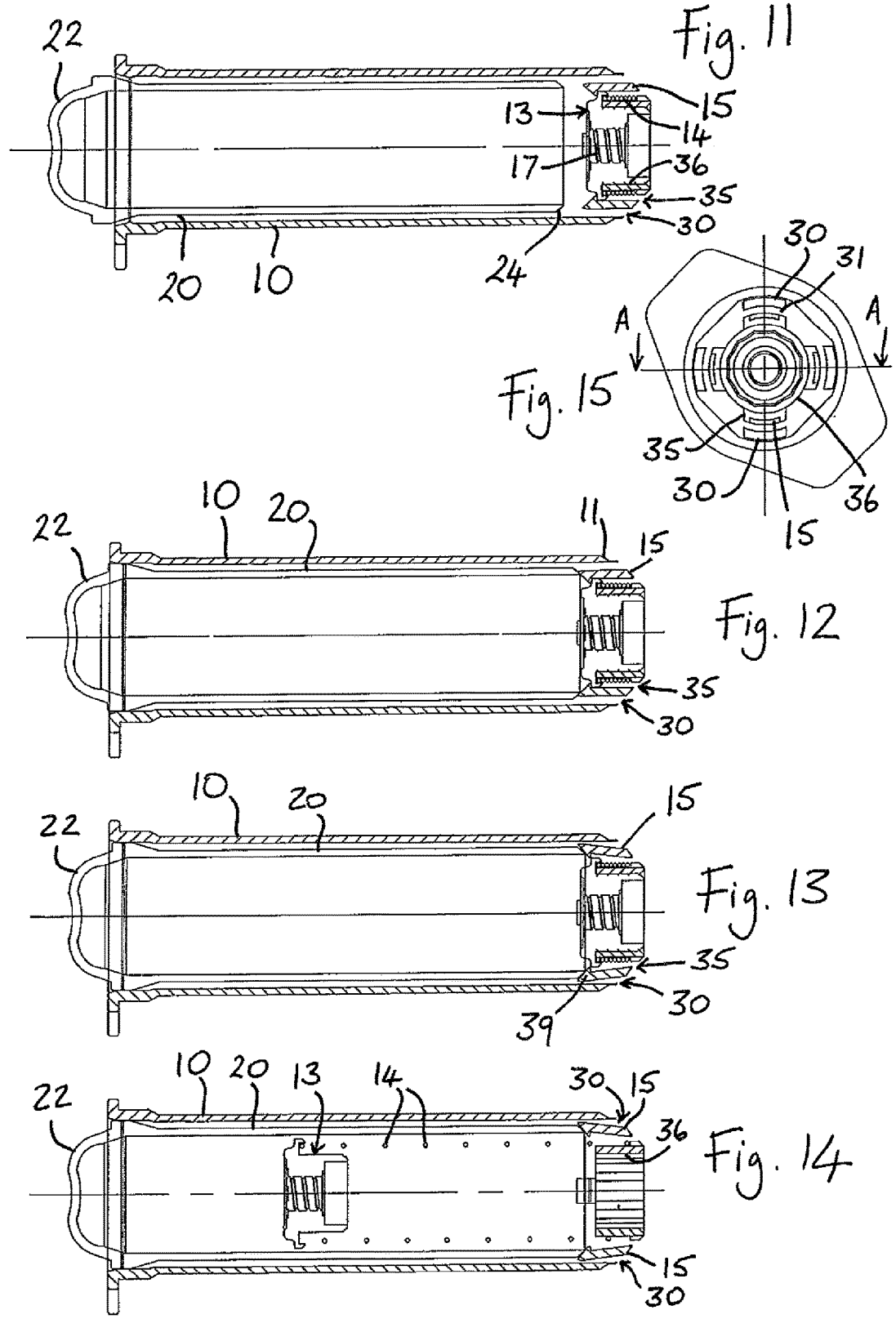

NEEDLE RETRACTION MEDICAL DEVICE

CROSS REFERENCE TO RELATED APPLICATIONS

This application is a national stage of International Application No. PCT/GB2016/050149, filed Jan. 25, 2016, which claims the benefit of GB Patent Application No. 1501317.0, filed Jan. 27, 2015.

TECHNICAL FIELD

This invention concerns a needle retraction device which may form part of or consist of either a syringe for injection of fluid into a human or animal body or a body fluid sampler, which is used for withdrawal of sample fluid from a human or animal body. In either case the device is provided with a mechanism for automatic needle retraction in order that the needle and a needle carrying hub are retracted, immediately following use, into a hollow plunger which is inserted into a main hollow body of the device to avoid the risk of needle-stick injury to users and other personnel. In the case of a syringe the same plunger may also serves for expression of the injectable fluid just prior to needle retraction.

BACKGROUND

Needle-stick accidents are particularly prevalent and carry a high risk of infection in the field of phlebotomy (blood sampling). There is also a risk of needle-stick injuries during the use of syringes for injection of fluids. Syringes and blood samplers with provision for automatic needle retraction are disclosed in the applicant's earlier specification WO 92/018187. These devices, and other design variants subsequently developed, comprise a tubular hollow body of suitable plastics material in one end of which plural deflectable latches are integrally formed for the purpose of mounting a needle hub against bias of a spring.

In use, a plunger having a hollow interior and a closed rear end is inserted into the hollow body and pushed inwards until its front end forces apart the deflectable latches to release the spring, which drives the hub and an attached needle assembly rearwards into the interior of the plunger. This is now a well-known manner of automatically retracting and encapsulating a needle. All that is required is the insertion and full depression of the plunger. However, in some circumstances, the force required to be applied to the plunger in order to deflect the latches outwards and bring about needle retraction is considered unacceptably high. For example, single-handed operation of the device is preferable and not all relevant medical staff have sufficiently strong hands to manipulate with ease. It is, in any event, desirable to reduce the force required to trigger needle retraction in such devices in order to achieve smoother operation.

The preferred material for the hollow body of such devices is polypropylene owing to its good strength and suitability for moulding, particularly resistance to shrinkage during moulding. For this reason, and other reasons related to detailed standards set for production and operation criteria for such medical devices, it is not possible to change the material. It is also important that the latches do not lose required strength/stiffness for the initial retention of the needle hub against spring bias, including during application of needle point load during use of the device.

The deflectable latches are formed integrally with the hollow body, that is to say they are moulded in one piece. The latches extend longitudinally inside the hollow body from body walling at or adjacent a first end of the body. In the production process for certain known devices of the applicant a respective opening is formed radially inwards of each of the latches.

BRIEF SUMMARY OF THE DISCLOSURE

With aforesaid object in view, of reducing the force required to trigger needle retraction, the present invention provides a needle retraction medical device comprising a hollow body having a first end and a second end, said first end being provided with a needle mounting hub and with a plurality of releasable latches holding said needle mounting hub against spring bias, the latches being formed integrally with the hollow body and projecting longitudinally inside the hollow body from a proximal end at or adjacent the first end of the hollow body to a free end, and a respective opening being provided in the body radially inwards of each of the latches, and a plunger having a forward end insertable into the body from the second end, a hollow interior and a closed rear end, said plunger front end being operable, upon insertion of the plunger into the body, to deflect the latches radially outwards and thereby release the needle mounting hub from the latches so that the hub together with the needle mounted thereby retract under spring action into the hollow interior of the plunger, characterised in that a respective opening is also provided in the hollow body radially outwards of each of the latches so that each latch connects to the material of the body only at each side of its proximal end.

A further aspect of the invention is a hollow body prior to assembly with the needle hub and spring and plunger, but in other respects still having the features just specified.

The invention is applicable to syringes, blood samplers, other body fluid samplers and any other hollow body devices with needle retraction mechanisms.

The invention will be described further, by way of example, by reference to the accompanying drawings.

BRIEF DESCRIPTION OF THE DRAWINGS

FIG. 11 is a longitudinal cross-section through the same embodiment of the assembled blood sampler device of the invention as shown in FIGS. 6 to 10, along line A-A of FIG. 15 and prior to actuation of the retraction mechanism;

FIGS. 12 to 14 are views comparable to FIG. 11 showing the sequence of operation of the device as retraction of the needle hub takes place;

FIG. 15 is an end view of the assembled blood sampler device shown in FIG. 11 (and in FIGS. 7 to 10);

DETAILED DESCRIPTION

Figure 1:
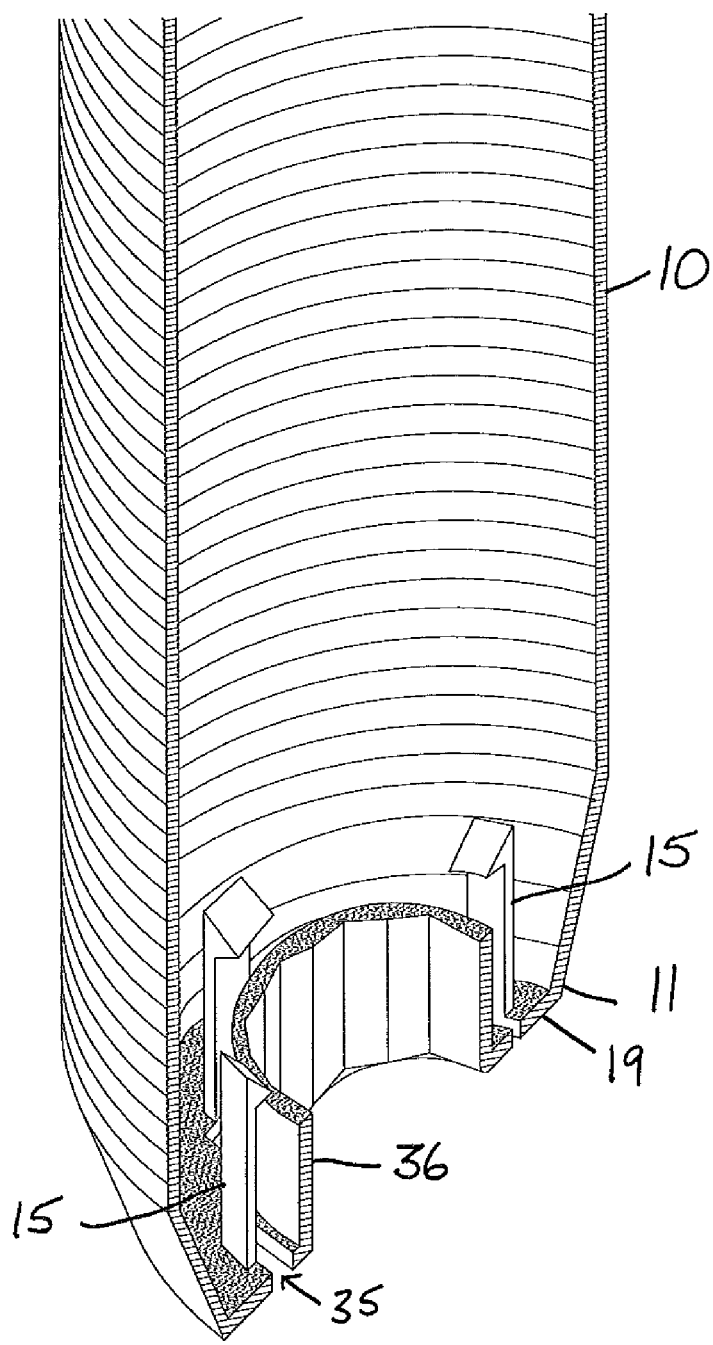
FIG. 1 is a partial perspective view of a cross-section through a hollow body of a prior art blood sampler device.

First of all the conventional parts of a known automatic needle retraction blood sampling needle holder will be described with reference to FIGS. 1 to 16. The same reference numerals are used throughout the drawings to designate corresponding parts.

The needle holder comprises a tubular hollow body 10 having a first end 11, in which a needle mounting hub 13 is mounted against bias of a spring 14 by means of plural deflectable latches 15, and a second open end 16. When the device is to be used a known needle assembly (not shown), as used in phlebotomy, is secured into the hub 13 by screw threaded engagement in a threaded central bore 17 of the hub. Typically, a first needle of this assembly extends outwards and is used to enter the vein of a patient while a second needle, or an inner end of the same needle, extends axially into the hollow body 10 and an evacuated blood collection vial is placed into the hollow body, a septum of same being pierced by the inwardly extending needle tip so that blood will be collected into the vial. When sampling is complete and the vial is removed, a plunger 20 having a hollow interior and a closed rear end 22 is inserted into the hollow body 10 and pushed inwards, as shown in the operation sequence of FIGS. 11 to 14 and also the sequence of FIGS. 3 to 5 and FIGS. 8 to 10, until its front end 24 forces apart the deflectable latches 15 to release the spring 14. This drives the hub 13 and attached needle assembly (not shown) rearwards into the interior of the plunger 20 to the position shown in FIGS. 5, 10 and 14.

As shown four latches 15 are arranged at 90° spacing around the interior of the first end of the hollow body 10. These latches 15 are moulded in one piece with the body 10 and extend longitudinally in the interior of the body from a proximal end attached to the body 10, specifically to an end wall 19 of the body, to a free end which is formed with a retaining enlargement 39. The enlargement 39 is of conventional wedge shaped form, providing a shoulder 38 behind which a flange 33 of the needle hub 13 engages as well as a sloping actuating surface 37 which is engaged by the front end 24 of the plunger 20 two bring about retraction of the needle hub in the operation outlined above.

As shown, a cylindrical wall 36 extends inwards from the inner periphery of the end wall 19 of the hollow body 10 as location means for the needle hub 13 and the spring 14.

In producing the hollow body 10 by moulding in one piece from suitable plastics material with integral end wall 19, inner wall 36 and latches 15, openings 35 are formed radially inwards of each latch 15, as shown in FIGS. 1 to 5. These openings 35, which are narrow slots, extending in annular direction immediately to inner side of each latch 15, are produced by a tool which fashions the latch in the moulding process. In this particular embodiment these openings 35 are shown as extending annularly beyond the sides of the proximal end or root of each latch 15. In other embodiments such openings may not extend beyond the side edges of the respective latches.

Figure 2:
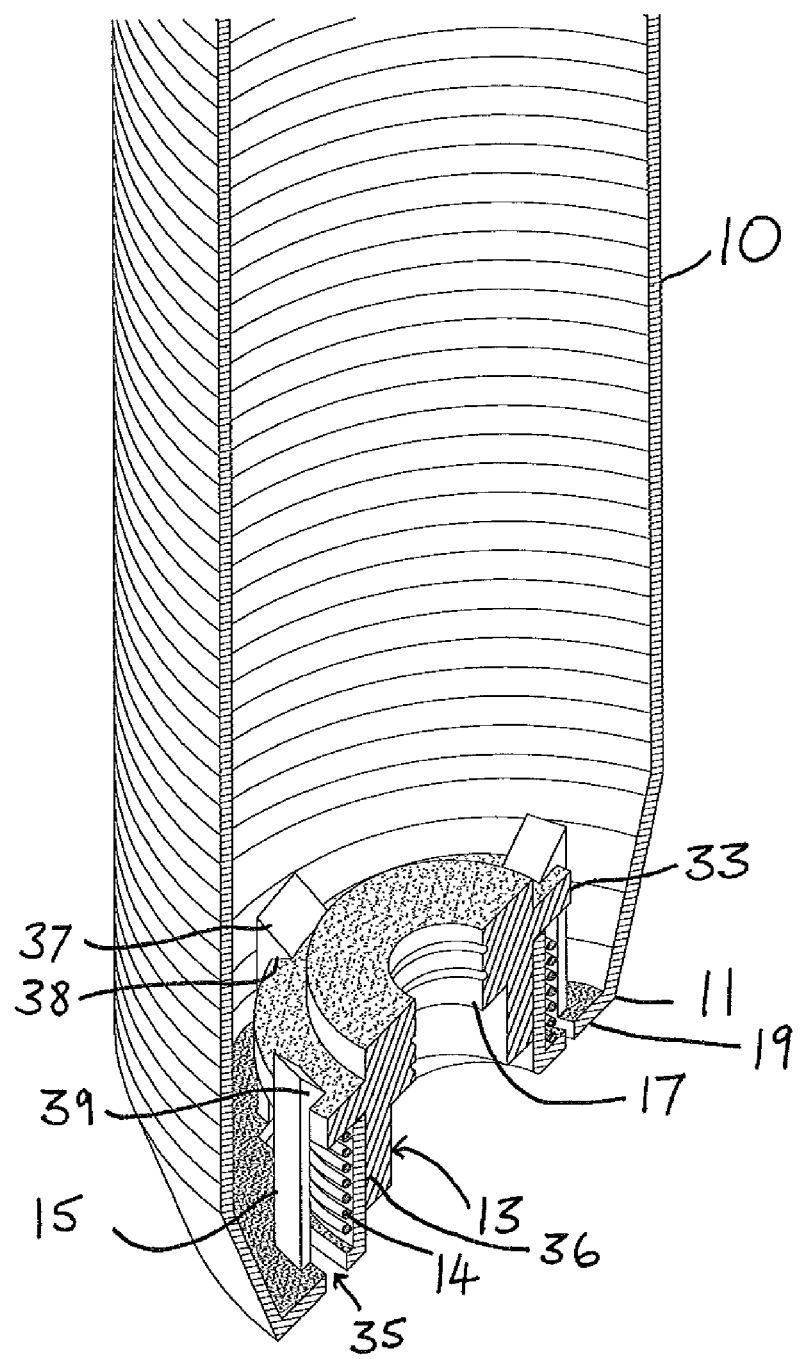
FIG. 2 is the same view of the same prior art device as in FIG. 1, but showing a spring biased needle hub mounted into the hollow body as in the assembled blood sampler device.
Figure 3:
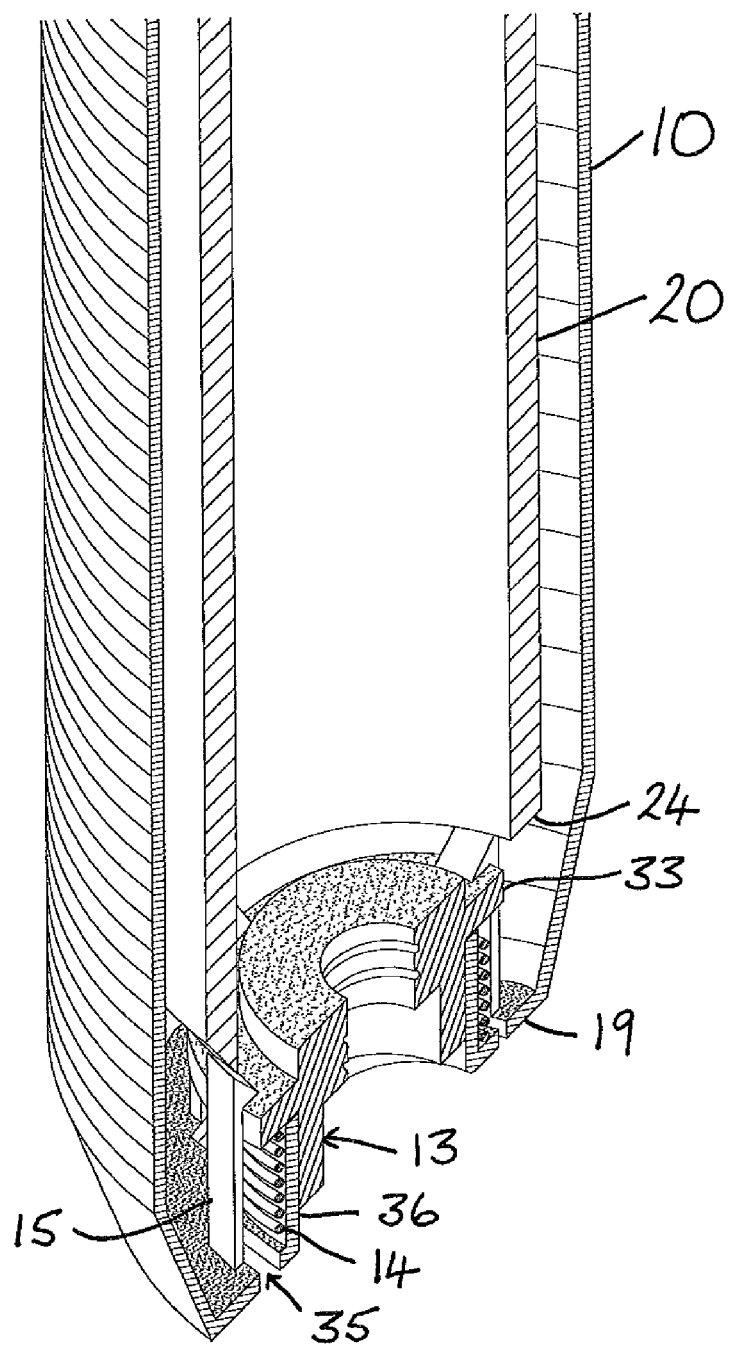
FIG. 3 is the same view of the same prior art device as in FIG. 2, but additionally showing a front end of a plunger inserted into the body of the device just prior to actuation of the needle hub retraction mechanism.
Figure 7:
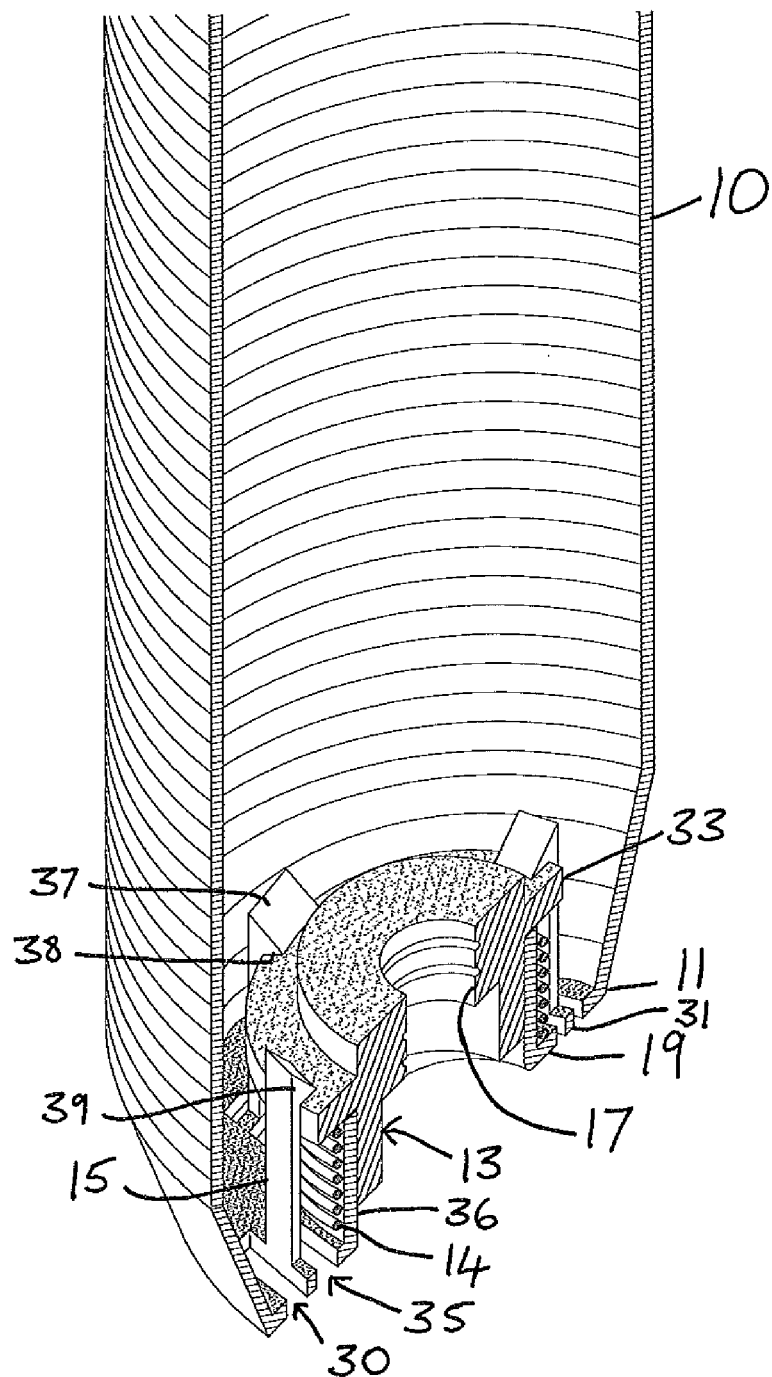
Figure 8:
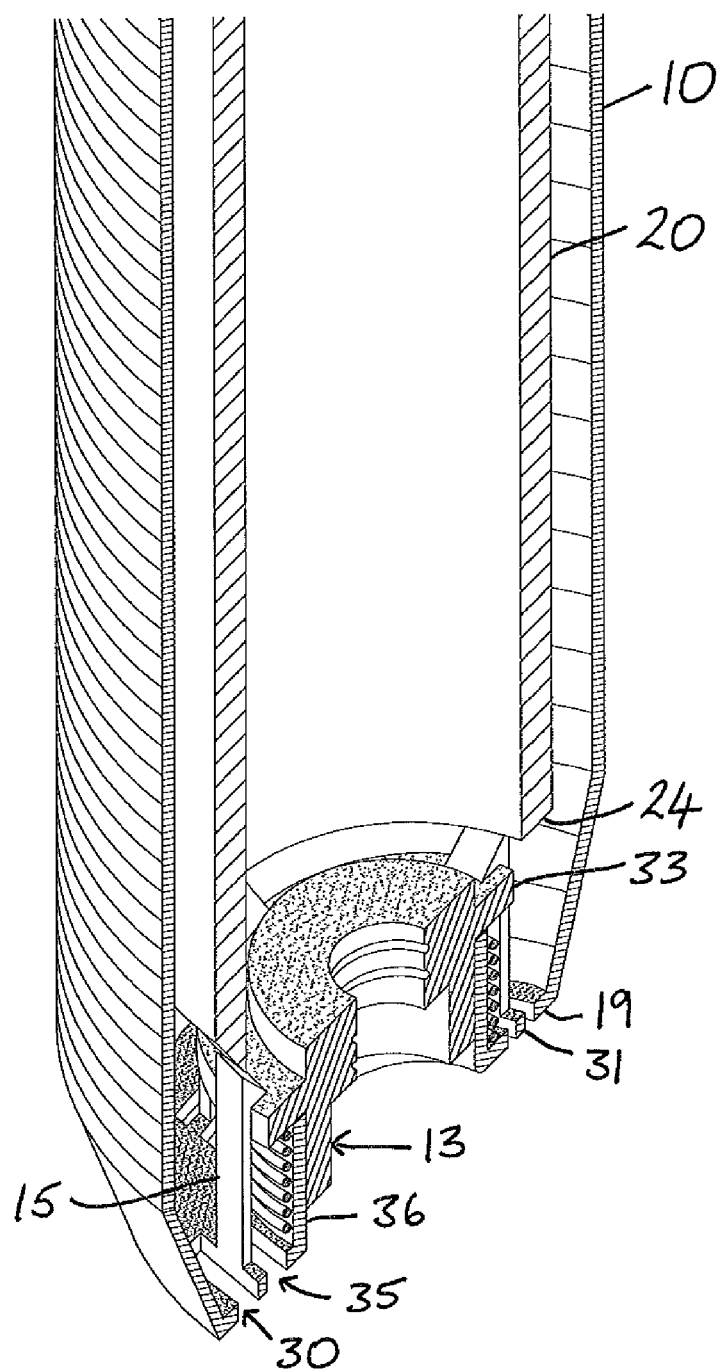

Initially the latches 15 extend from the end wall 19 substantially parallel to the outer walling and axis of the hollow body 10. An annular flange 33 of the needle hub 13 seats on the upper edge of the wall 36 with the helical spring 14 located around the outside of the wall 36 and held under compression below the flange 33, as best shown in FIGS. 2 and 7.

In use, the latches 15 are deflected outwards upon engagement of their actuating surfaces 37 by the front end 24 of the plunger 20 and further application of force as the plunger is pushed further inwards into the hollow body 10.

Figure 4:
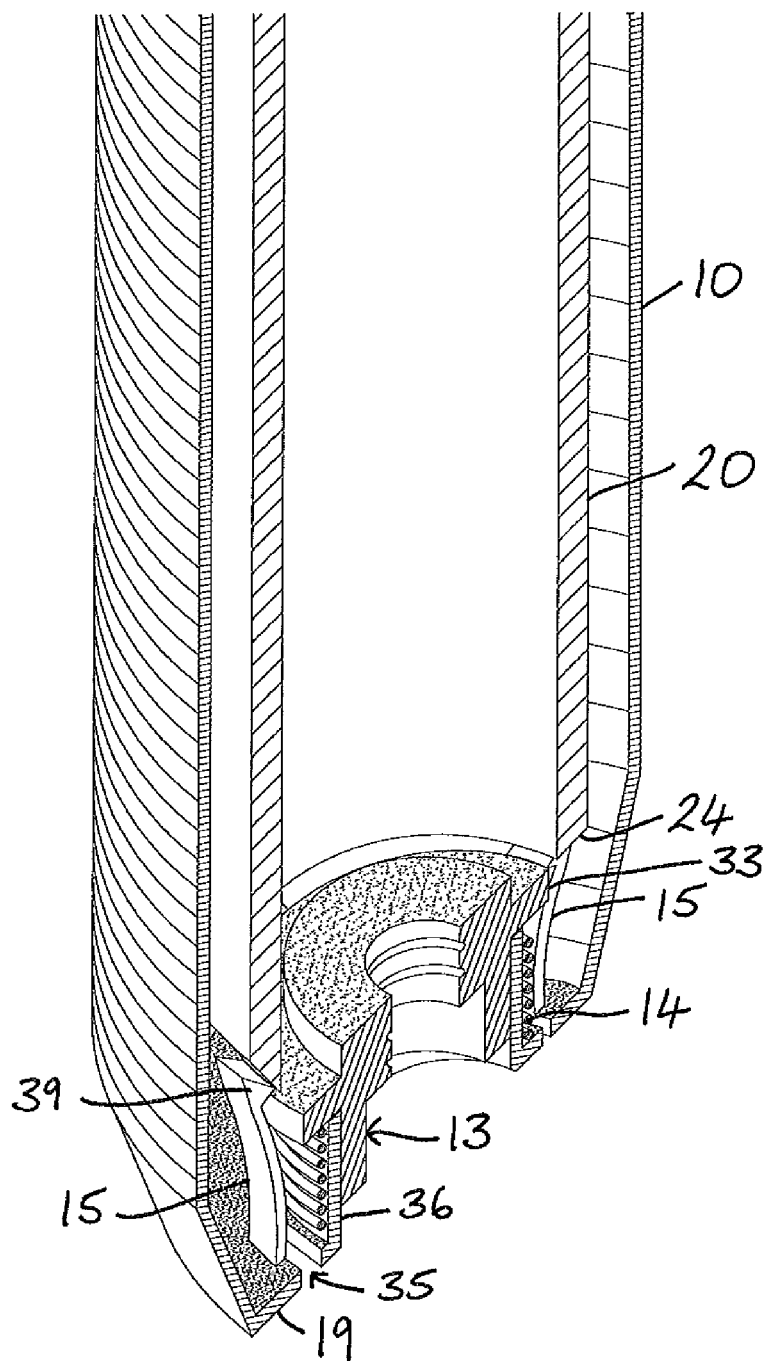
FIG. 4 shows the same prior art device as pressure is exerted on the plunger to deflect the latches.
Figure 5:
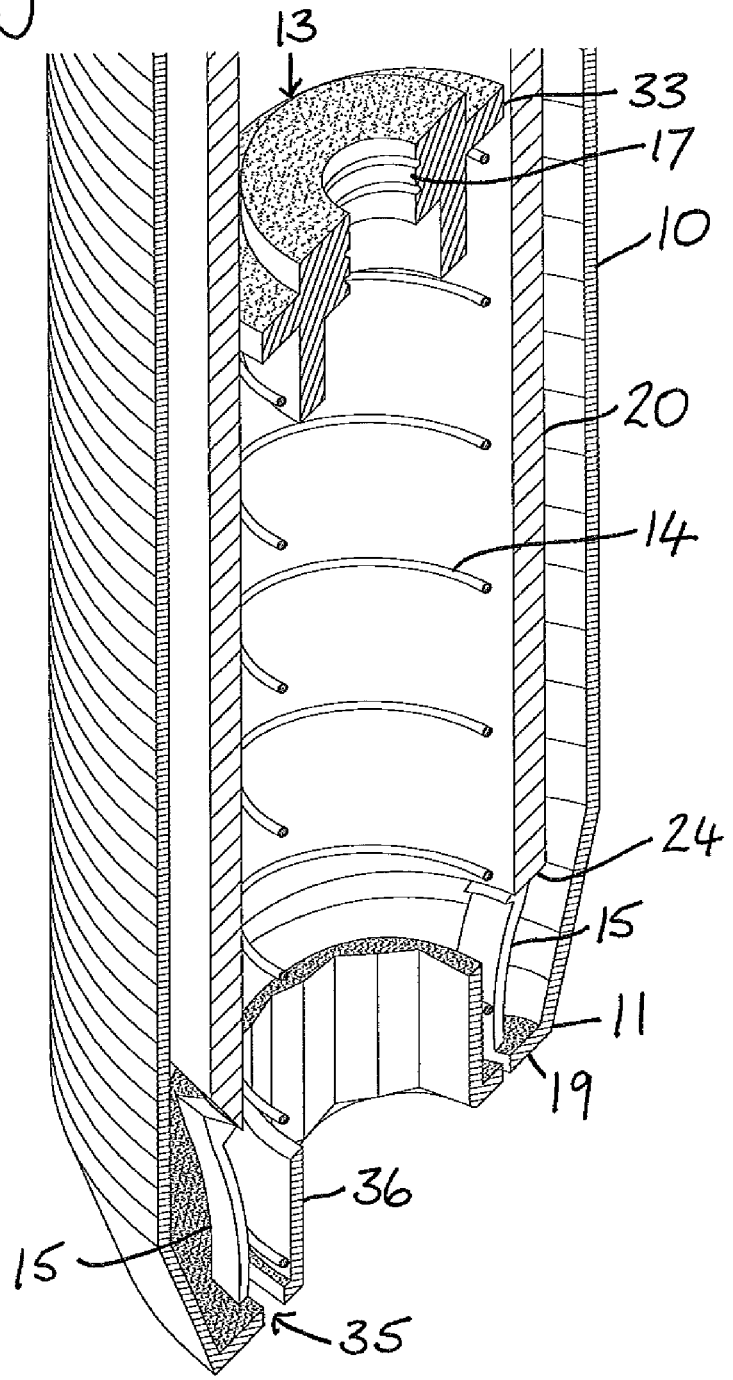
FIG. 5 shows the same prior art device after the spring has been released and the needle hub has been retracted into the interior of the plunger.
Figure 6:
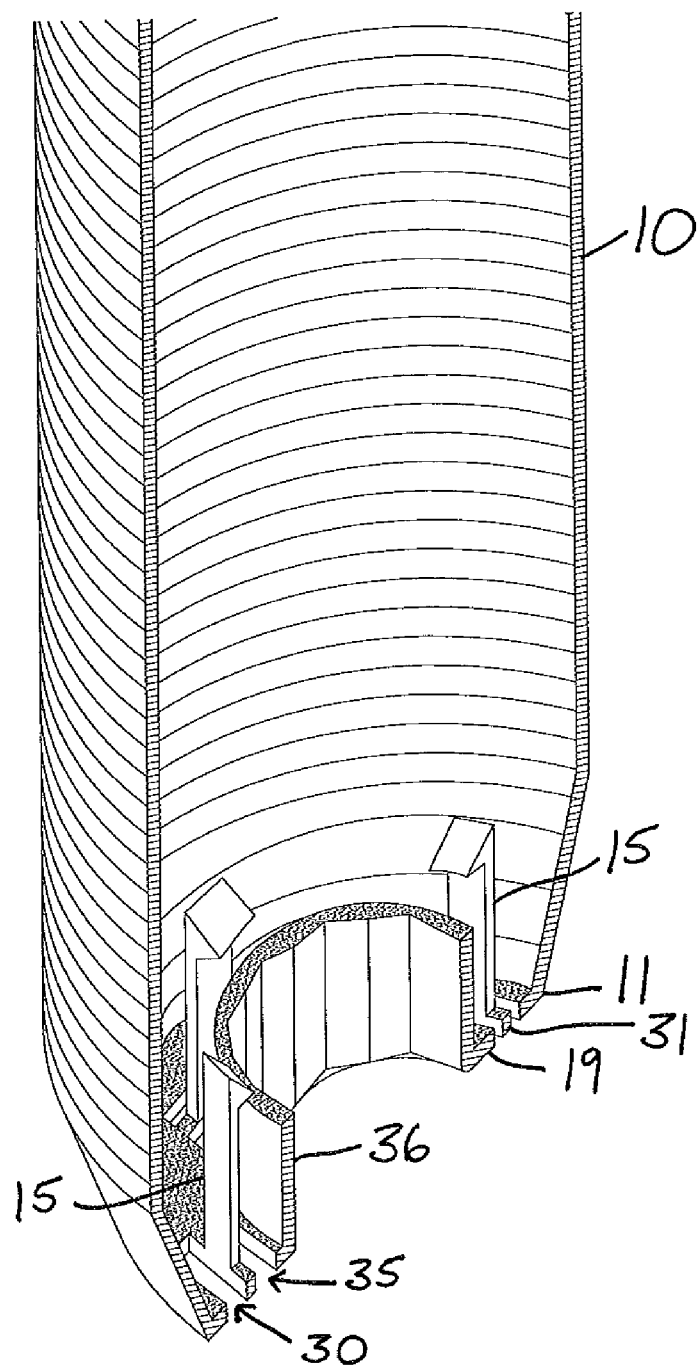
FIGS. 6 to 10 are views corresponding to FIGS. 1 to 5, but showing the hollow body and needle retraction mechanism in accordance with a first practical embodiment in accordance with the present invention.

In the prior art device illustrated in FIGS. 1 to 5 of the drawings, the deflection of the latches 15, as shown in FIGS. 4 and 5, is by bending of same in an outwardly curving manner from their initial upstanding position.

In accordance with the invention, in the embodiment illustrated in FIGS. 6 to 10 and also in FIGS. 11 to 15, an additional opening 30 in the end wall 19 of the hollow body 10 is provided radially outwardly of each latch 15. These openings 30 are also in the form of narrow slots extending in an annular direction. Also, in the illustrated embodiment, these openings 30 extend annularly beyond the sides of the proximal end or root of each latch 15. In other embodiments such openings may not extend beyond the side edges of the respective latches. Thus, in embodiments in accordance with the invention, there are openings 35, 30, both inside and outside the proximal end of each latch 15 so each latch is connected only at the respective sides (or side edges) of its proximal end. In this illustrated embodiment, because both the openings 30, 35 extend annually beyond the sides of the respective latches 15, the connection to the main part of the end wall 19 is provided by a short rectangular cross-sectional strap 31.

Figure 9:
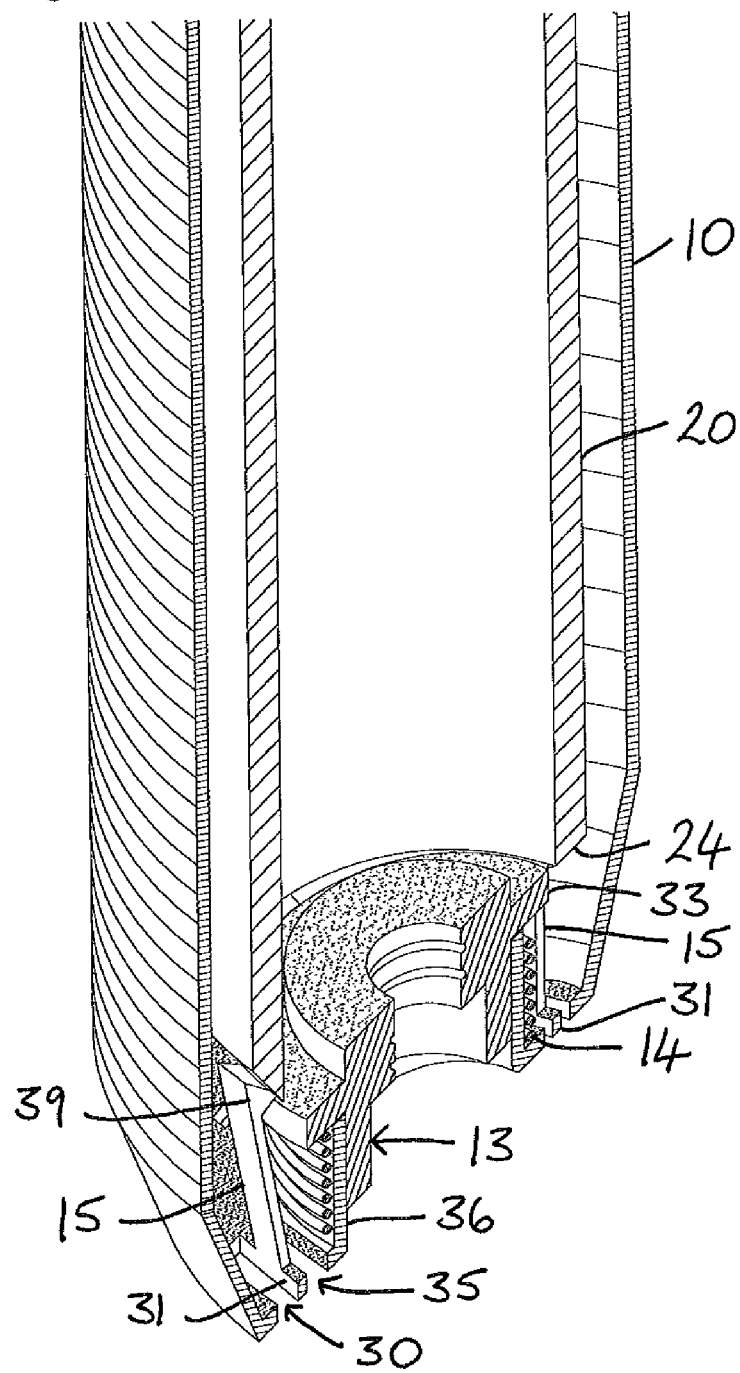
Figure 10:
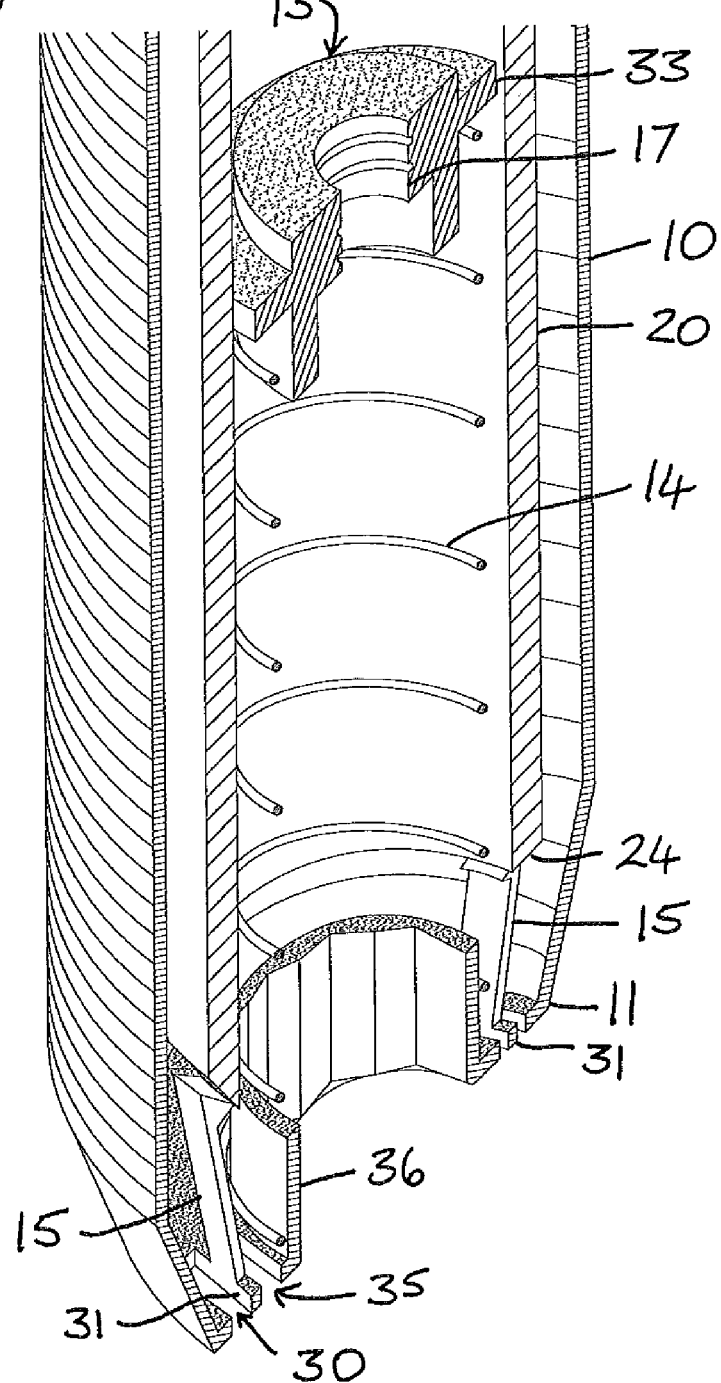
Figure 16:
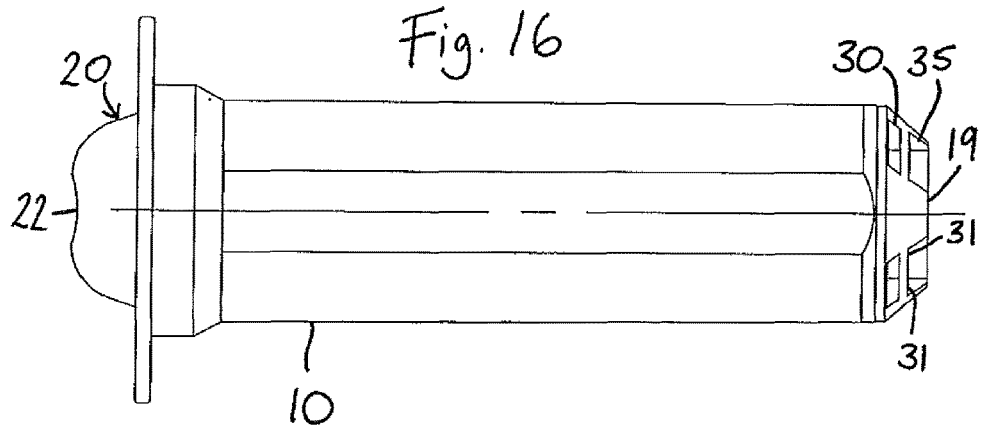
FIG. 16 is a side view, to an enlarged scale compared to FIGS. 11 to 15, of the assembled blood sampler device in the needle hub retracted condition shown in FIG. 14.

Thus, in the embodiment of the invention, as illustrated in FIGS. 6 to 15, the deflection of the latches 15 is by a twisting of these connecting straps 31. The material of the upstanding latches 15 is not bent but remains substantially straight, merely inclined outwards relative to the axis of the body 10, as best shown in FIGS. 9 and 10. Such deflection requires less forced to accomplish and it has been found that the force required for such deflection may be up to 75% less than force required for deflection by bending of the latch as in the prior art structure.

Figure 17A:
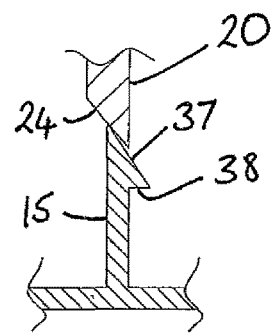
FIGS. 17a to 17c are schematic side and perspective views of a latch in a prior art needle retraction device.
Figure 17B:
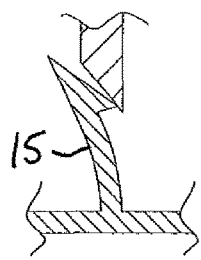
Figure 17C:
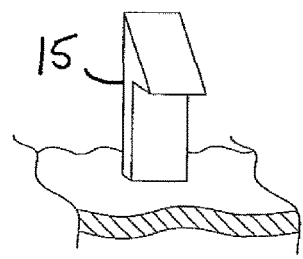
Figure 18A:
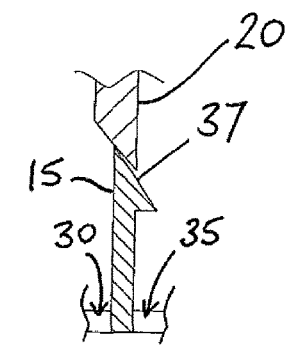
FIGS. 18a to 18c are corresponding schematic side and perspective views of a latch in a needle retraction device in accordance with the present invention.
Figure 18B:
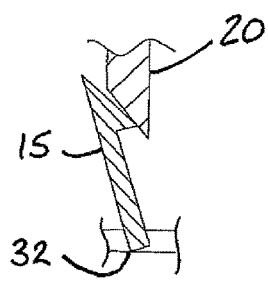
Figure 18C:
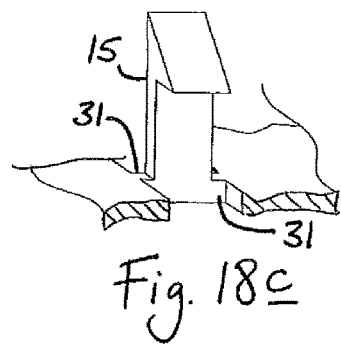

FIGS. 17 and 18 illustrate in enlarged detail the contrast between the manner of deflection in a prior art device (FIG. 17) and a device in accordance with the invention as exemplified by the embodiment of FIGS. 6 to 16 FIG. 18. In the prior art device the proximal end of the latch is shown connected on all sides to the material of the hollow body, namely projecting upwards from a continuous web of plastics material, and the latch 15 when engaged by the actuating end 24 of the plunger 20 is deflected by bending of the material forming the latch 15. In the device in accordance with the invention, material is removed both in front and behind the latch (openings 35 and 30) so that it is connected to the web of plastics material only at the side edges by way of the connecting strap 31. This results in the latch deflecting as though it is pivoting along a hinge line at its base, along the rear edge 32, namely the edge opposite the actuating surface 37 where the force of the plunger 20 is applied, as indicated in FIG. 18b. The material of the upstanding latch 15 is not deformed, as by bending in the prior art, as the deformation only takes effect at the connections at the respective sides of the base of the latch. As shown, these connections may advantageously be provided as short rectangular connector portions or straps 31 by extending the respective openings 30, 35 beyond the side edges of the base of the latch 15, as already noted in the above description of the illustrated embodiment of blood sampler device. These connecting straps 31 twist to bring about the deflection of the latch 15.

Figure 19:
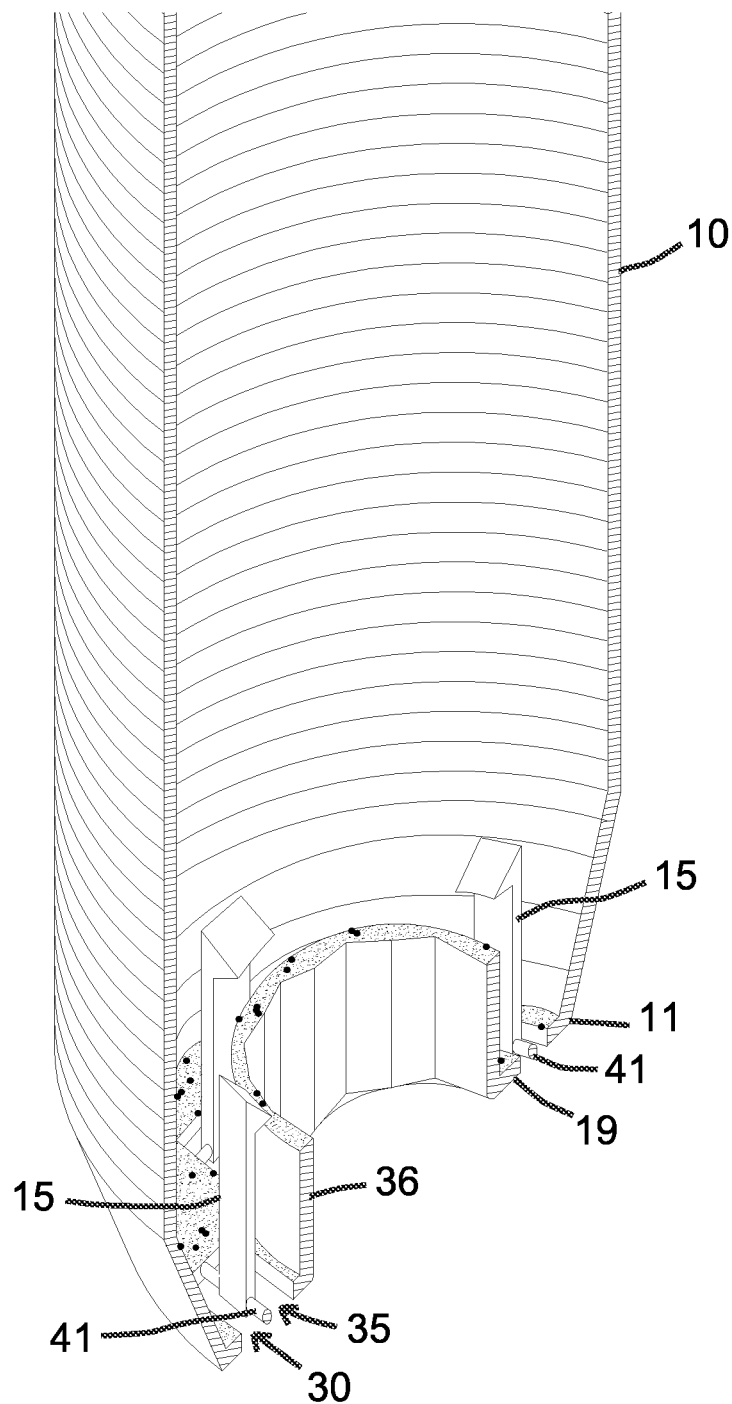
FIGS. 19 and 20 are view corresponding to FIGS. 6 and 10, namely partial perspective views of a cross-section of a hollow body and needle retraction mechanism, but in this case in accordance with a modified, second practical embodiment of the invention where the connecting strap is of a cylindrical shape.
Figure 20:
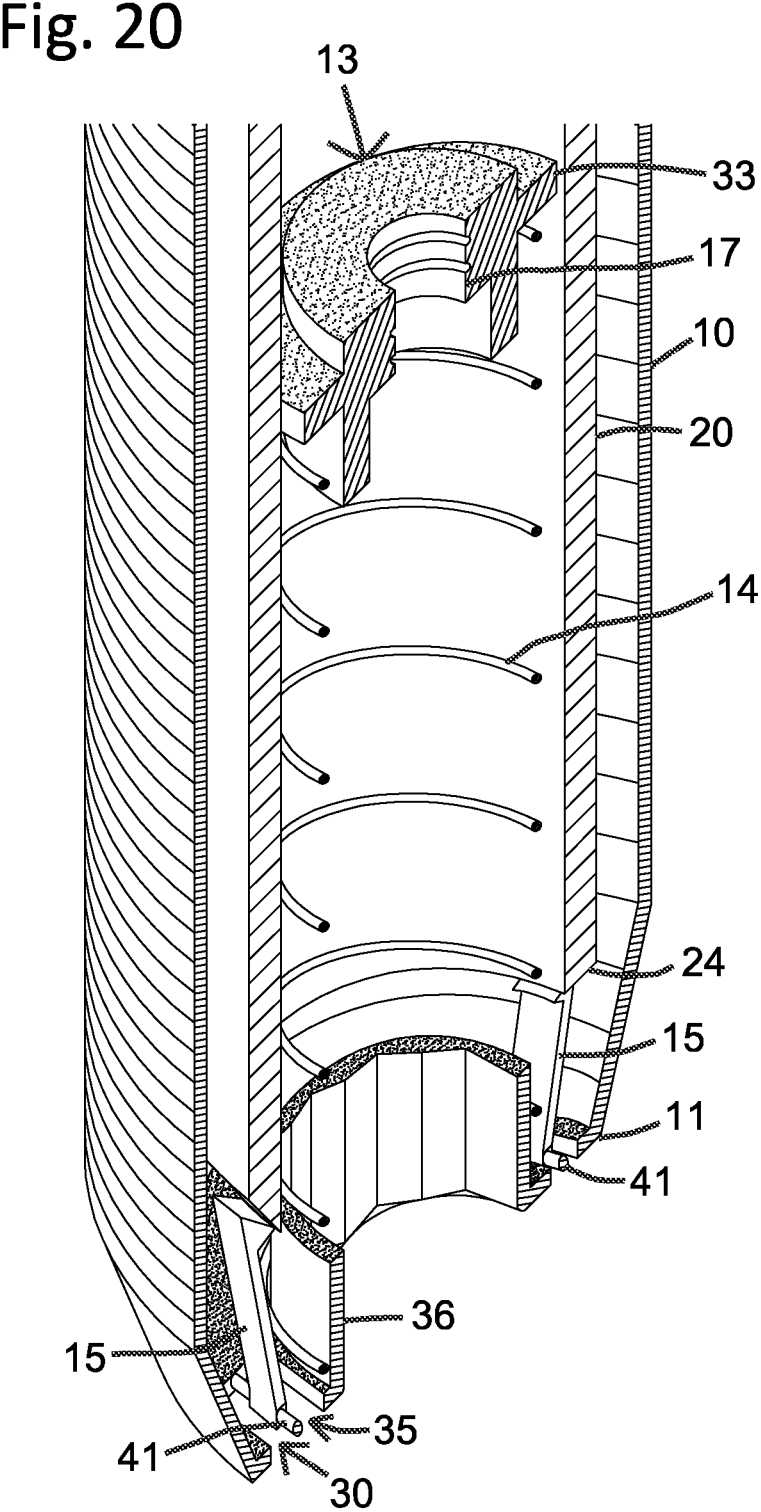
Figure 21:
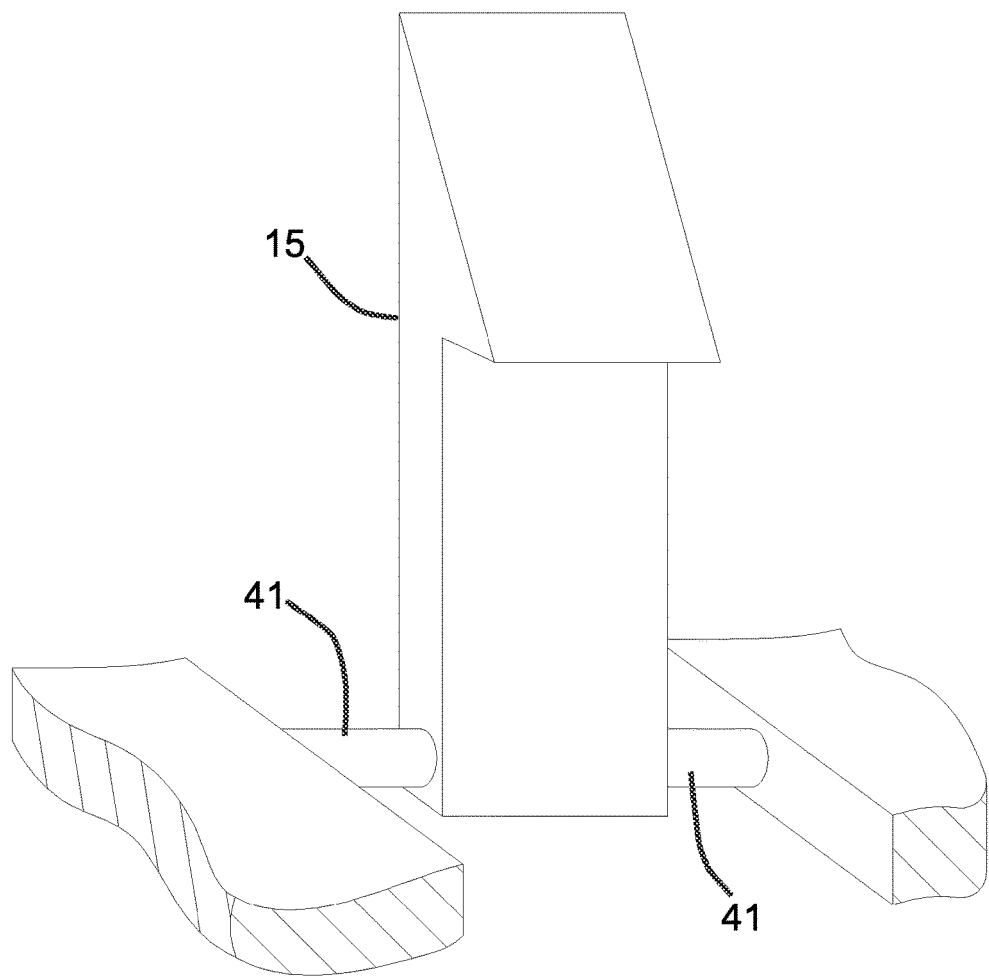
FIG. 21 is a view corresponding to FIG. 18c, namely an enlarged detail perspective view of a latch in a needle retraction device in accordance with the second embodiment.

In a modified embodiment, illustrated in FIGS. 19 to 21, each connecting strap 41 has a cylindrical shape, i.e. a rounded cross-section, as opposed to the square or rectangle I cross section featured in the embodiment of FIGS. 6-10. The strap 41 is connecting the latch 15 to the main part of the end wall 19 in the same manner as strap 31 with openings 35, 30 both inside and outside the proximal end of each latch 15. The deflection of the latches 15 is by a twisting of these connecting straps 41. The material of the upstanding latches 15 is not bent, but remains substantially straight, merely inclined outwards relative to the axis of the body, as best shown in FIG. 20. The modified cylindrical shape of the strap 41 further reduces the force required to release the latches 15, typically to less than ⅔ of force required with the rectangular shape of connective strap 31.

In other embodiments, the details may vary. Moreover, as noted, the invention is applicable to any other hollow body needle retraction mechanism.

The invention claimed is:

1. A needle retraction medical device comprising a hollow body having a first end and a second end, said first end being provided with a needle mounting hub and with a plurality of releasable latches holding said needle mounting hub against spring bias, the latches being formed integrally with the hollow body and projecting longitudinally inside the hollow body from a proximal end at or adjacent the first end of the hollow body to a free end, and a respective opening being provided in the body radially inwards of each of the latches, and a plunger having a forward end insertable into the body from the second end, a hollow interior and a closed rear end, said plunger front end being operable, upon insertion of the plunger into the body, to deflect the latches radially outwards and thereby release the needle mounting hub from the latches so that the hub together with the needle mounted thereby retract under spring action into the hollow interior of the plunger, wherein a respective opening is also provided in the hollow body radially outwards of at least some of the latches so that each such latch connects to the material of the body only at each side of its proximal end,
wherein the openings which lie radially outwards of the latches and the openings which lie radially inwards of those latches extend beyond the proximal ends of the latches in each annular direction, thereby providing connecting straps which mount each such latch to the hollow body and which are capable of twisting to effect deflection of the latch.

2. A device according to claim 1 wherein the latches each have radially inwardly directed retaining formations at their free end.

3. A device according to claim 2 wherein the retaining formations of the latches provide latching shoulders for engagement of the needle hub.

4. A device according claim 1 wherein the latches each have sloping actuating surfaces at their free end.

5. A device according to claim 1 wherein at least the openings which lie radially outwards of the latches extend beyond the proximal ends of the latches in each annular direction.

6. A device according to claim 1 wherein the connecting straps are of substantially rectangular cross-section.

7. A device according to claim 1 wherein the connecting straps are of substantially circular cross-section.

8. A device according to claim 1 wherein the latches are provided at equally-angular spacing around the interior of the hollow body.

9. A device according to claim 1 wherein four latches are provided in the hollow body.

10. A needle retraction medical device comprising a hollow body having a first end and a second end, said first end being provided with a plurality of releasable latches for holding a needle mounting hub against spring bias, the latches being formed integrally with the hollow body and projecting longitudinally inside the hollow body from a proximal end at or adjacent the first end of the hollow body to a free end, and a respective opening being provided in the first end of the body radially inwards of each of the latches, wherein a respective opening is also provided in the hollow body radially outwards of at least some of the latches so that each such latch connects to the material of the body only at each side of its proximal end,
wherein the openings which lie radially outwards of the latches and the openings which lie radially inwards of those latches extend beyond the proximal ends of the latches in each annular direction, thereby providing connecting straps which mount each such latch to the hollow body and which are capable of twisting to effect deflection of the latch.

11. A device according to claim 10 wherein the latches each have radially inwardly directed retaining formations at their free end.

12. A device according to claim 11 wherein the retaining formations of the latches provide latching shoulders for engagement of the needle hub.

13. A device according to claim 10 wherein the latches each have sloping actuating surfaces at their free end.

14. A device according to claim 10 wherein at least the openings which lie radially outwards of the latches extend beyond the proximal ends of the latches in each annular direction.

15. A device according to claim 10 wherein the connecting straps are of substantially rectangular cross-section.

16. A device according to claim 10 wherein the connecting straps are of substantially circular cross-section.

17. A device according to claim 10 wherein the latches are provided at equally-angular spacing around the interior of the hollow body.

18. A device according to claim 10 wherein four latches are provided in the hollow body.

* * * * *